United States Patent [19]

Nakada et al.

[11] Patent Number: 5,714,368

[45] Date of Patent: Feb. 3, 1998

[54] THERMOSTABLE NON-REDUCING SACCHARIDE-FORMING ENZYME ITS PRODUCTION AND USES

[75] Inventors: Tetsuya Nakada; Hiroto Chaen; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 466,434

[22] Filed: Jun. 6, 1995

[30] Foreign Application Priority Data

Jun. 24, 1994 [JP] Japan ................... 6-166011

[51] Int. Cl.$^6$ ................... C12N 9/26; C12N 9/24; C12N 9/14; C12N 9/10
[52] U.S. Cl. ................... 435/201; 435/200; 435/100; 435/101; 536/123.13; 536/124; 514/53; 514/54; 514/60
[58] Field of Search ................... 435/100, 101, 435/200, 201; 536/123.13, 124; 514/53, 54, 60

[56] References Cited

U.S. PATENT DOCUMENTS

| | | | |
|---|---|---|---|
| 4,521,252 | 6/1985 | Miyake et al. | 127/46.3 |
| 4,762,857 | 8/1988 | Bollin, Jr. et al. | 514/777 |
| 4,839,164 | 6/1989 | Smith | 424/64 |
| 5,026,566 | 6/1991 | Roser | 426/443 |
| 5,455,168 | 10/1995 | Maruta et al. | 435/201 |

FOREIGN PATENT DOCUMENTS

| | | |
|---|---|---|
| 0558213 | 9/1993 | European Pat. Off. . |
| 0606753 | 7/1994 | European Pat. Off. . |
| 50-154485 | 12/1975 | Japan . |
| 5823799 | 2/1983 | Japan . |
| 5872597 | 4/1983 | Japan . |
| 58-216695 | 12/1983 | Japan . |
| 2106912 | 4/1983 | United Kingdom . |
| 92/03565 | 3/1992 | WIPO . |

OTHER PUBLICATIONS

Chemical Abstracts 117:22222k (1992).
ATCC Catalogue of Bacteria & Bacteriophages, 17th Ed., 1989, p. 248.
L. Lama et al, "Thermostable amylolytic activity from Sulfolobus solfataricus", Biotec Forum Europe, vol. 8, No. 1, 2 Feb. 1991, pp. 201–203.
"Catalogue of Bacteria and Phages", Amer. Type Cult. Collec., 18th Edit., p. 363, (1992).
Handbook of Amylases and Related Enzymes, Their Sources, Isolation Methods, Properties and Applications, pp. 18–63, Wheaton & Co., Ltd. (press) (1988).
"Current Status of Starch Application Development and Related Problems", Food Chemicals, pp. 67–72 (1992).

*Primary Examiner*—Leon B. Lankford, Jr.
*Assistant Examiner*—Francisco C. Prats
*Attorney, Agent, or Firm*—Browdy and Neimark

[57] ABSTRACT

Disclosed are novel thermostable non-reducing saccharides-forming enzyme, its preparation and uses. The enzyme is obtainable from the culture of microorganisms such as *Sulfolobus acidocaldarius* (ATCC 33909 and ATCC 49426) and *Sulfolobus solfataricus* (ATCC 35091 and ATCC 35092), and capable of forming non-reducing saccharides having a trehalose structure as an end unit when allowed to act on reducing partial starch hydrolysates at a temperature of over 55° C. Glucoamylase and α-glucosidase readily yield trehalose when allowed to act on the non-reducing saccharides. These non-reducing saccharides and trehalose are extensively useful in food products, cosmetics and pharmaceuticals.

23 Claims, 4 Drawing Sheets

5,714,368

THERMOSTABLE NON-REDUCING SACCHARIDE-FORMING ENZYME ITS PRODUCTION AND USES

BACKGROUND OF THE INVENTION

1. Field of the Invention

The present invention relates to a novel thermostable non-reducing saccharide-forming enzyme, and its preparation and uses, more particularly, to a novel thermostable non-reducing saccharide-forming enzyme which forms a non-reducing saccharide having a trehalose structure as an end unit when allowed to act on one or more reducing partial starch hydrolysates having a degree of glucose polymerization of 3 or higher, and to its preparation. The present invention further relates to a non-reducing saccharide having a trehalose structure as an end unit which is preparable by utilizing the thermostable non-reducing saccharide-forming enzyme and to a relatively-low reducing saccharide containing the non-reducing saccharide, as well as to a trehalose prepared from these saccharides and to a composition containing these non-reducing saccharides.

2. Description of the Prior Art

Trehalose or α, α-trehalose is known as a non-reducing saccharide consisting of glucose units. As described in Advance in *Carbohydrate Chemistry*, Vol.18, pp.201–225 (1963), published by Academic Press, USA, and in *Applied and Environmental Microbiology*, Vol.56, pp.3,213–3,215 (1990), trehalose widely exists in microorganisms, mushrooms, insects, etc., through the content is relatively low. Since trehalose is a non-reducing saccharides, it does neither induce the amino-carbonyl reaction with the substances containing amino groups such as amino acids and proteins nor alter amino acid-containing substances. Thus, trehalose is expected to be used without fear of causing an unsatisfiable browning and deterioration. Because of these, it has been in great demand to establish an industrial-scale preparation of trehalose.

In conventional preparation of trehalose, as disclosed in Japanese Patent Laid-Open No.154,485/75, microorganisms are utilized, or as proposed in Japanese Patent Laid-Open No.216,695/83, maltose is converted into trehalose by using maltose- and trehalose-phosphorylases in combination. The former, however, is not suitable for industrial-scale preparation because the content of trehalose present in microorganisms as a starting material is usually lower than 15 w/w % (the wording "w/w %" will be abbreviated as "%" in the specification, unless specified otherwise), on a dry solid basis (d.s.b.), and the extraction and purification steps are complicated. The latter has not yet been realized as an industrial-scale preparation because of the following demerits: (i) maltose as a substrate could not be used at a relatively-high concentration because trehalose is formed via glucose phosphate; (ii) the yield of the objective trehalose is relatively low; (iii) it is substantially difficult to continue the enzymatic reactions smoothly while retaining their reaction systems stably.

As regards the preparation of trehalose, it is reported in the column titled "Oligosaccharides" in the chapter titled "Current Status of Starch Application Development and Related Problems" in *"Food Chemicals"*, pp.67–72 (August, 1992) that "In spite of a wide applicability of trehalose, an enzymatic preparation thereof via a direct saccharide-transfer reaction or a hydrolytic reaction has been reported to be scientifically almost impossible in this field." Thus, an enzymatic preparation of trehalose using starch as a material has been deemed to be scientifically difficult.

It is known that partial starch hydrolysate, prepared from starch as a material such as liquefied starch, cyclodextrins and maltooligosaccharide, usually have a reducing end-group as an end unit and exhibited reducibility. These partial starch hydrolysates are referred to as "non-reducing partial starch hydrolysates" in the present specification. The reducing power of such reducing partial starch hydrolysates is generally expressed by "Dextrose Equivalent (DE) value", based on their dry weight. It is known that among reducing partial starch hydrolysates those with a relatively-high DE value generally have a decreased molecular weight and viscosity and an increased appropriate sweetness and reactivity, and readily react with substances having amino groups such as amino acids and proteins to cause an unsatisfiable browning, smell and deterioration of their quality.

These unfavorable properties of reducing partial starch hydrolysates are varied depending on their DE values, and the relationship between reducing partial starch hydrolysates and their DE values is very important. It has been even believed to be impossible to set aside the relationship in this field.

The only way to break the relationship is a method to form non-reducing saccharides by hydrogenating reducing partial starch hydrolysates at a relatively-high pressure of hydrogen to convert their reducing end-groups into sugar alcohols. This method, however, requires a high-pressure autoclave and consumes large amounts of hydrogen and energy, as well as requiring a relatively-high level of control or safety facility to prevent disasters. The material reducing partial starch hydrolysates and the resultant products differ because the former consists of glucose units and the latter, i.e. sugar alcohols of the resultant partial starch hydrolysates, consists of glucose and sorbitol units. The sugar alcohols have some concern for causing temporary symptoms such as digestive disorder and diarrhea when administered to the body. Thus, it has been in great demand to establish a method to decrease or even eliminate the reducing power of reducing partial starch hydrolysates without changing glucose units as a constituent saccharide thereof.

Considering the aforementioned circumstances, the present inventors have energetically studied enzymes which are capable of forming saccharides having a trehalose structure when allowed to act on starch hydrolysates. As a result, the present inventors found that microorganisms of the genus Rhizobium, named as "Rhizobium sp. M-11", and microorganisms of the genus Arthrobactor, named as "Arthrobactor sp. Q36", isolated respectively from the soils as disclosed in Japanese Patent Application No.349,216/93, are capable of producing novel non-reducing saccharide-forming enzymes which form non-reducing saccharides having a trehalose structure as an end unit when allowed to act on reducing partial starch hydrolysates having a degree of glucose polymerization of 3 or higher, and found that trehalose is readily preparable by allowing glucoamylase or α-glucosidase to act on the non-reducing saccharides having a trehalose structure as an end unit obtainable by this novel enzymes.

Enzymes derived from the microorganisms of the genus Rhizobium or the genus Arthrobactor, however, are relatively-low in thermal stability. Thus, in case that these enzymes are utilized for preparing non-reducing saccharides having a trehalose structure as an end unit and trehalose, it is necessary to allow the enzymes to act on at a temperature of below 55° C. With regard to the temperature of enzymatic reaction, as described in the column titled "Enzymes related to saccharides" in the chapter titled "Enzymes related to saccharides and their applications" in *"Koso-Ouyou-no-*

*Chishiki*" (Knowledge on Enzyme Applications), the first edition, pp.80–129 (1986) that "In the conditions of industrial-scale enzymatic reactions for saccharification, the reactions at a temperature of below 55° C. involves a risk of contamination and a decrease of pH during the reaction", in long-time enzymatic reactions using starch as a material, when an enzyme is allowed to act on at a temperature of below 55° C., because of contamination and a decrease of pH of reaction mixtures which may inactivate the activity of such enzymes, and it is necessary to add lysozyme for the prevention of contamination and the pH control of the reaction mixtures. In addition, when the hydrolysis of partial starch hydrolysates is relatively low, insoluble substances may be formed due to retrogradation of starch. On the other hand, since a thermostable enzyme can act on at a relatively-high temperature, contamination during the enzymatic reaction is less concerned and the retrogradation of partial starch hydrolysates is hardly caused. Thus, it has been in great demand to establish novel preparations of non-reducing saccharides, having a trehalose structure as an end unit, and trehalose from such non-reducing saccharides by utilizing a thermostable non-reducing saccharide-forming enzyme capable of acting on at a temperature of over 55° C.

SUMMARY OF THE INVENTION

The present invention is to provide a novel preparation of a non-reducing saccharide from a reducing partial starch hydrolysate by utilizing a thermostable non-reducing saccharide-forming enzyme, as well as to provide such a non-reducing saccharide and its uses.

To attain the aforementioned object, the present inventors have extensively screened microorganisms capable of producing a novel thermostable non-reducing saccharide-forming enzyme, which forms non-reducing saccharides having a trehalose structure when allowed to act on reducing partial starch hydrolysates. As a result, the present inventors found that microorganisms of the genus Sulfolobus, named as "*Sulfolobus acidocaldarius*" ATCC 33909 and ATCC 49426, and as "*Sulfolobus solfataricus*" ATCC 35091 and ATCC 35092, produce a novel thermostable non-reducing saccharide-forming enzyme which forms a non-reducing saccharide having a trehalose structure as an end unit when allowed to act on reducing partial starch hydrolysates and also is stable up to a temperature of about 85° C., and found that the non-reducing saccharide can be readily prepared at the objective temperature of over 55° C. when the thermostable enzyme is allowed to act on reducing partial starch hydrolysates. The present inventors also found that trehalose is readily preparable by first allowing the thermostable enzyme to act on reducing partial starch hydrolysates, then subjecting the resultant non-reducing saccharides to the action of glucoamylase or α-glucosidase. Thus, the present inventors accomplished this invention. Also, the present inventors established preparations of compositions such as food products, cosmetics and pharmaceuticals which contain the present non-reducing saccharides, relatively-low reducing saccharides containing the same and/or trehalose, and accomplished this invention.

BRIEF EXPLANATION OF THE ACCOMPANYING DRAWINGS

DETAILED DESCRIPTION OF THE INVENTION

Figure 1:
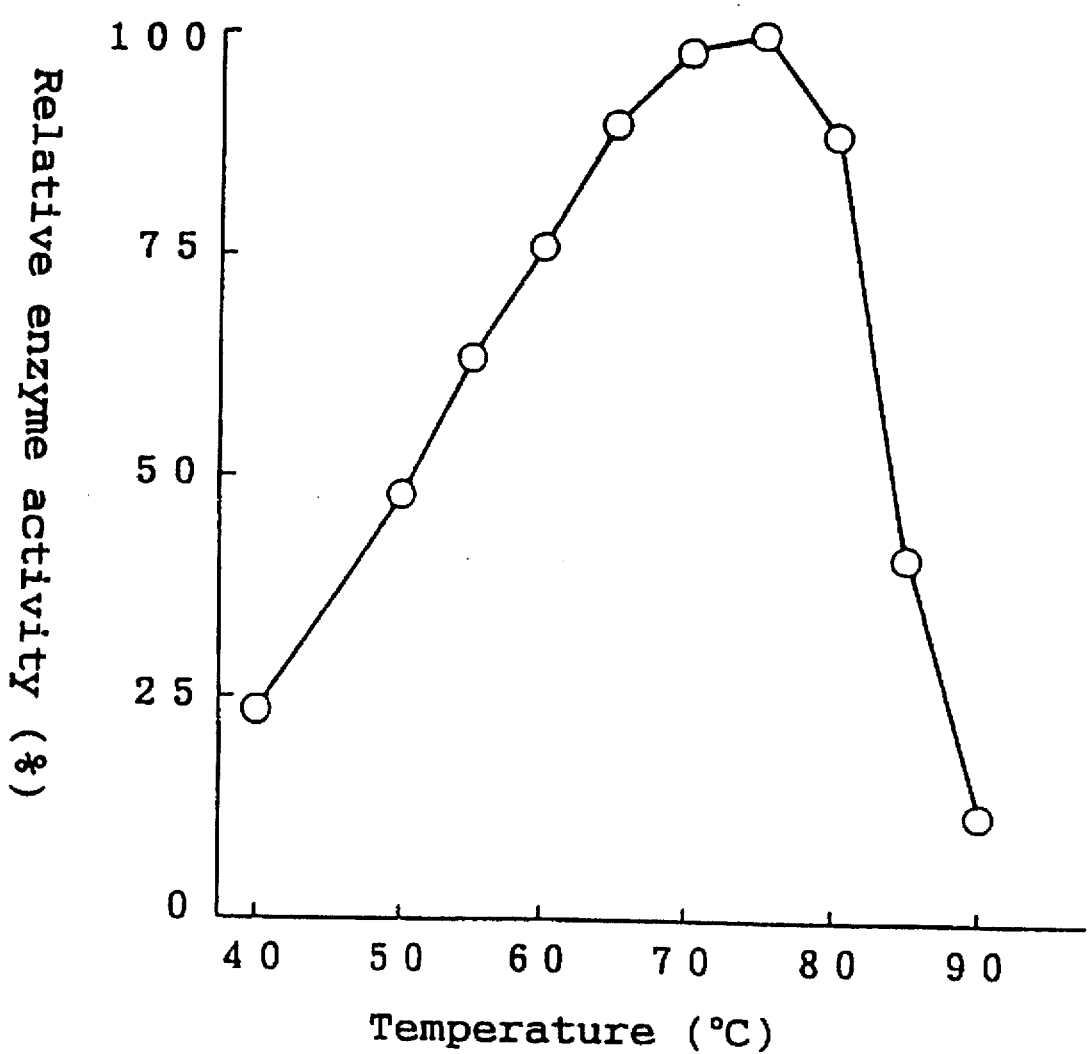
FIG. 1 shows the influence of temperature on the activity of the thermostable non-reducing saccharide-forming enzyme of the present invention.

The present invention relates to a novel thermostable non-reducing saccharide-forming enzyme, and its preparation and uses. The present invention further relates to a microorganism capable of producing said enzyme, non-reducing saccharides prepared with said enzyme, relatively-low reducing saccharides containing said non-reducing saccharides, trehalose prepared from these saccharides, and compositions containing either or both of these non-reducing saccharides and trehalose.

The present inventors have extensively screened microorganism capable of producing a novel thermostable non-reducing saccharide-forming enzyme which forms non-reducing saccharides having a trehalose structure when allowed to act on reducing partial starch hydrolysates, and eventually found the objective microorganisms.

In the present specification, unless specified otherwise, a novel thermostable non-reducing saccharide-forming enzyme, which forms a non-reducing saccharide having a trehalose structure as an end unit when allowed to act on reducing partial starch hydrolysates and acts on at a temperature of over 55° C., is referred to as a thermostable non-reducing saccharide-forming enzyme.

Now, the present inventors found that microorganisms of the genus Sulfolobus, named as "*Sulfolobus acidocaldarius*" ATCC 33909 and ATCC 49426, and as "*Sulfolobus solfataricus*" ATCC 35091 and ATCC 35092, are capable of producing a novel thermostable non-reducing saccharide-forming enzyme.

In addition to the above-mentioned microorganisms, other strains of the genus Sulfolobus and their mutants can be suitably used in the present invention as long as they produce the present thermostable non-reducing saccharide-forming enzyme which forms the non-reducing saccharide having a trehalose structure as an end unit when allowed to act on reducing partial starch hydrolysates.

Any nutrient culture medium can be used in the invention as long as these microorganisms can grow therein and produce the present non-reducing saccharide-forming enzyme: For example, synthetic- and natural-nutrient culture media can be used as the nutrient culture medium. Any carbon-containing substance can be used in the invention as a carbon source as long as it is utilized by the microorganisms: Examples of such a carbon source are saccharides such as glucose, fructose, lactose, sucrose, mannitol, sorbitol, molasses and reducing partial starch hydrolysates; and organic acids such as citric acid, succinic acid and their salts. The concentrations of these carbon sources in nutrient culture media are appropriately chosen. For example, in the case of using reducing partial starch hydrolysates, a preferable concentration is usually 20% or lower, more particularly, 5% or lower, d.s.b., in view of the growth of the microorganisms. The nitrogen sources usable in the present invention are, for example, inorganic nitrogen compounds such as ammonium salts and nitrates; and organic nitrogen-containing substances such as urea, corn steep liquor, casein, peptone yeast extract and beef extract. The inorganic ingredients usable in the invention are, for example, calcium salts, magnesium salts, potassium salts, sodium salts, phosphates and other salts of manganese, zinc, iron, copper, molybdenum and cobalt.

The microorganisms usable in the invention are cultured under aerobic conditions at a temperature, usually, in the range of 40°–95° C., preferably, in the range of 50°–90° C.; and at a pH in the range of 2–7, preferably a pH in the range of 2–6. The cultivation time used in the invention is set to a time required for the growth initiation of the microorganisms preferably, 10–100 hours. The concentration of dissolved oxygen is nutrient culture media is not specifically restricted, but usually in the range of 0.5–20 ppm. For keeping the dissolved oxygen in nutrient culture media, the means of controlling of aeration stirring, aeration with oxygen, and increasing the inner pressure of a fermenter can be utilized. The cultivation is carried out batchwise or in continuous manner.

After completion of the cultivation, the present enzyme is recovered from the cultures. The activity of the present enzyme is found mainly in cells. It is preferable to purify these cells in usual manner and to use the resultant as a crude enzyme preparation. For example, a partially purified enzyme preparation which is almost free of concomitant enzymes, can be prepared by dialyzing a crude enzyme preparation which had been prepared by salting out a crude enzyme solution with ammonium sulfate and concentrating the resultant; and successively purifying the dialyzed solution on anion-exchange column chromatography using "DEAE TOYOPEARL®", an anion-exchange resin; hydrophobic column chromatography using "BUTYL TOYOPEARL®", a hydrophobic resin, all of which are products of Tosoh Corporation, Tokyo, Japan. Furthermore a purified enzyme preparation exhibiting an electrophoretically single band can be prepared by applying the partially purified enzyme preparation to gel filtration chromatography using "ULTROGEL AcA 44®", a resin for gel filtration which is a product of Sepracor Inc., Marlborough, Mass. 01752, U.S.A.; and anion-exchange column chromatography using "MONO Q®", an anion-exchange resin which is a product of Pharmacis LKB, Uppsala, Sweden.

The present thermostable non-reducing saccharide-forming enzyme thus obtained has the following physicochemical properties:

(1) Action

Forming a non-reducing saccharide having a trehalose structure as an end unit when allowed to act on one or more reducing partial starch hydrolysates having a degree of glucose polymerization of 3 or higher;

(2) Molecular weight

About 69,000 to 79,000 daltons on sodium dodecylsulfate-polyacrylamide gel electrophoresis (SDS-PAGE);

(3) Isoelectric point (pI)

About 5.4 to 6.4 on isoelectrophoresis using ampholyte;

(4) Optimum temperature

About 75° C. when incubated at pH 5.5 for 60 min;

(5) Optimum pH

About 5.0 to 5.5 when incubated at 60° C. for 60 min;

(6) Thermal stability

Stable up to a temperature of about 85° C. when incubated at pH 7.0 for 60 min; and (7) pH stability Stable at a pH of about 4.0 to 9.5 when incubated at 25° C. for 16 hours.

The activity of the present thermostable non-reducing saccharide-forming enzyme is assayed as follows: One ml of an enzyme solution is added to 4 ml of 1.25 w/v % maltopentaose in 20 mM phosphate buffer (pH 5.5) as a substrate, and the mixture solution is incubated at 60° C. for 60 min. The reaction mixture is heated at 100° C. for 30 min to suspend the enzymatic reaction, and the reaction mixture is precisely diluted by 10 times with deionized water, followed by determining the reducing power of the diluted solution on the Somogyi-Nelson's method. As a control, an enzyme solution, which had been heated at 100° C. for 30 min to inactivate the enzyme, is treated similarly as above. The enzyme solution is mixed with copper liquor to suspend the enzymatic reaction, followed by determining the reducing power of the solution on the Somogyi-Nelson's method. With such a determination, one unit activity of the present enzyme is defined as the amount of enzyme which diminishes the reducing power of that of one micromole of maltopentaose per minute.

Reducing partial starch hydrolysates, which can be used as a substrate for the present enzyme, are those prepared by partially hydrolyzing amylaceous substances such as starch, amylopectin and amylose by amylases or acids. Such reducing partial starch hydrolysates can be prepared by the hydrolysis using amylases include reducing partial starch hydrolysates prepared by hydrolyzing amylaceous substances with α-amylase, maltotriose forming amylase, maltotetraose forming amylase, maltopentaose forming amylase and maltohexaose forming amylase as disclosed in *Handbook of Amylases and Related Enzymes*, published by Pergamon Press, Tokyo, Japan (1988). In the case of preparing the reducing partial starch hydrolysates, debranching enzymes such as pullulanase and isoamylase can be arbitrarily used. One or more maltooligosaccharides such as maltotriose, maltotetraose, maltopentaose, maltohexaose and maltoheptaose can be favorably used as a reducing partial starch hydrolysate.

The concentration of the reducing partial starch hydrolysates used as a substrate in the invention is not specifically restricted. While the present enzymatic reaction proceeds even with a 0.1% solution of a substrate, the enzymatic reaction more favorably proceeds with solutions having a concentration of 2% or higher, preferably, those having a concentration of 5–50% of a substrate, d.s.b. Under these concentrations non-reducing saccharides having a trehalose structure are readily formed in a satisfactorily-high yield. The reaction temperature used in the present invention enzymatic reaction can be set to a temperature at which the present enzyme is not inactivated, i.e. a temperature up to about 85° C., preferably, a temperature in the range of 55°–70° C. The reaction pH used in the present enzymatic reaction is controlled to in the range of 3–9, preferably, in the range of about 4–7. The reaction time used in the present enzymatic reaction is adequately chosen depending on the conditions of the enzymatic reaction, generally, in the range of 0.1–100 hours in the case of using enzyme in an amount of about 0.1–100 units/g substrate, d.s.b.

The resultant reaction mixtures containing non-reducing saccharides have a reducing power much lower than those of the material reducing partial starch hydrolysates used as a substrate. For example, in the case of using maltopentaose as a substrate, about 75% of the initial reducing power diminishes or the reducing power of the present reaction mixtures lowers to about 25% with respect to the initial reducing power.

The resultant reaction mixtures are in usual manner subjected to filtration and centrifugation to remove insoluble substances, and the resultant solutions are decolored with an activated charcoal, desalted with ion exchangers in H- and OH-form, and concentrated into syrupy products which can be dried into powdery products. If necessary, the powdery products can be readily prepared into non-reducing saccharides with the highest possible purity by purifying the powdery products with one or more methods, for example, column chromatographic fractionations such as ion-exchange column chromatography, column chromatography using an activated charcoal or a silica gel; separations using organic acids such as alcohols and acetone; and fermentation with yeasts or alkaline treatments to decompose and remove the remaining reducing saccharides.

More particularly, ion-exchange column chromatography can be used in the invention as an industrial-scale preparation of the objective saccharides. The objective non-reducing saccharides with an improved purity can be arbitrarily prepared by, for example, column chromatography using a strongly-acidic cation exchange resin as described in Japanese Patent Laid-Open Nos.23,799/83 and 72,598/83 to remove concomitant saccharides. In this case, any one of fixed-bed, moving bed, and pseudo-moving methods can be employed.

If necessary, the present non-reducing saccharides having a trehalose structure thus obtained or relatively-low reducing saccharides containing the non-reducing saccharides can be hydrolyzed by amylases such as α-amylase, β-amylase, glucoamylase and α-glucosidase to control their sweetness and reducing power or to lower their viscosity; and the resultant products can be further treated with processings of hydrogenating the remaining reducing saccharides into sugar alcohols to diminish their reducing power.

More particularly, trehalose is readily prepared by allowing glucoamylase or α-glucosidase to act on the present non-reducing saccharides or relatively-low reducing saccharides containing them. A high trehalose content fraction is obtained by allowing glucoamylase or α-glucosidase to act on these saccharides to form a mixture of trehalose and glucose, and subjecting the mixture to the aforementioned purification such as ion-exchange column chromatography to remove glucose. The high trehalose content fraction can be arbitrarily purified and concentrated into a syrupy product, and, if necessary, the syrupy product can be further concentrated into a supersaturated solution, followed by crystallizing it into hydrous- or anhydrous-crystalline trehalose and recovering the resultant crystal.

To prepare hydrous crystalline trehalose, an about 65–90% solution of trehalose with a purity of about 60% or higher, d.s.b., is placed in a crystallizer, and gradually cooled while stirring in the presence of 0.1–20% seed crystal at a temperature of 95° C. or lower, preferably, at a temperature in the range of 10°–90° C., to obtain a massecuite containing hydrous crystalline trehalose. Also, the continuous crystallization to prepare hydrous crystalline trehalose while concentrating a solution of trehalose under reduced pressure can be favorably used in the present invention. Conventional methods such as separation, block pulverization, fluidized-bed granulation and spray drying can be employed in the present invention to prepare from the massecuite hydrous crystalline trehalose or crystalline saccharides containing it.

In the case of separation, massecuites are usually subjected to a basket-type centrifuge to separate hydrous crystalline trehalose from the mother liquor, and, if necessary, the hydrous crystalline trehalose is washed by spraying thereto with a small amount of cold water to facilitate the preparation of hydrous crystalline trehalose with an increased purity. In the case of spray drying, crystalline saccharides with no or substantially free of hygroscopicity are readily prepared by spraying massecuites with a concentration of 60–85%, d.s.b., and a crystallization percentage of about 20–60%, d.s.b., from a nozzle by a high-pressure pump; drying the resultant products with a 60°–100° C. hot air which does not melt the resultant crystalline powders; and aging the resultant powders for about 1–20 hours while blowing thereto a 30°–60° C. hot air. In the case of block pulverization, crystalline saccharides with no or substantially free of hygroscopicity are readily prepared by allowing massecuites with a moisture content of 10–20% and a crystallization percentage of about 10–60%, d.s.b., to stand for a period from about several hours to 3 days to crystallize and solidify the whole contents into blocks; and pulverizing or cutting the resultant blocks.

Although anhydrous crystalline trehalose can be prepared by drying hydrous crystalline trehalose to convert it into anhydrous one, it is generally prepared by providing a high trehalose content solution with a moisture content less than 10%; placing the solution in a crystallizer; keeping the solution in the presence of a seed crystal at a temperature in the range of 50°–160° C., preferably, a temperature in the range of 80°–140° C. under stirring conditions to obtain a massecuite containing anhydrous crystalline trehalose; and crystallizing and pulverizing anhydrous crystalline trehalose by conventional methods such as block pulverization, fluidized-bed granulation and spray drying.

The resultant non-reducing saccharides and relatively-low reducing saccharides containing them according to the present invention have a relatively-lower reducing power and a relatively-higher stability than those of the material reducing partial starch hydrolysates, and because of such properties, these saccharides can be mixed and processed with other materials, especially, amino acids and amino acid-containing substances such as oligopeptides and proteins without fear of causing an unsatisfiable browning, smell and deterioration of the materials. Unlike reducing partial starch hydrolysates, these saccharides have a relatively-low reducing power and viscosity, and, among these saccharides, those with a relatively-low degree of average glucose polymerization have a satisfactorily-higher quality and more mild sweetness than those of the hydrolysates.

The present non-reducing saccharides are hydrolyzed by amylases such as α-amylase derived from pancreas into relatively-low molecular weight non-reducing oligosaccharides or maltooligosaccharides, and these oligosaccharides are readily hydrolyzed by α-glucosidase and intestinal enzymes into glucose and trehalose molecules. The resultant trehalose is readily hydrolyzed by trehalase into glucose. Thus, the present non-reducing saccharides and relatively-low reducing saccharides containing them, as well as trehalose, can be utilized as an energy source by the body when orally administered. These present saccharides and trehalose are not substantially fermented by dental carries-inducing microorganisms, and this renders them useful as a dental carries-preventing sweetener. These saccharides and trehalose have properties such as osmotic pressure-controlling ability, filler-imparting ability, gloss-imparting ability, moisture-retaining ability, viscosity-imparting ability, ability to prevent crystallization of other saccharides, substantial no fermentability, and ability to present retrogradation of gelatinized starch.

The present trehalose can be utilized parenterally as a liquid feeding and infusion without fear of toxicity and side effect, preferably, utilized as an energy source by the body. Also, the present trehalose has a satisfiable stability and sweetness, and those in crystalline form can be arbitrarily used as a sugar coating material for tablets in combination with binders such as pullulan, hydroxyethyl starch and polyvinylpyrrolidone.

Anhydrous crystalline trehalose can be arbitrarily used as a desiccant for food products, cosmetics, pharmaceuticals, and their materials and intermediates, and readily formed into compositions in the form of powder, granule and tablet with a satisfactory stability and quality.

Thus, the present non-reducing saccharides and relatively-low reducing saccharides containing them, as well as trehalose prepared from these saccharides, can be arbitrarily used as a sweetener, taste-improving agent, quality-improving agent, stabilizer, excipient and desiccant in a variety of compositions such as food products, tobaccos, cigarettes, feeds, pet foods, cosmetics and pharmaceuticals.

The present non-reducing saccharides and relatively-low reducing saccharides containing them, as well as trehalose prepared from these saccharides, can be used intact as a seasoning for sweetening. If necessary, they can be used together with adequate amounts of one or more other sweeteners, for example, powdered syrup, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrocharcone, stevioside, α-glycosyl stevioside, rebaudioside, glycyrrhizin, L-aspartyl L-phenylalanine methyl ester, saccharin, glycine and alanine; and/or a filler such as dextrin, starch and lactose.

The present non-reducing saccharides and relatively-low reducing saccharides containing them, as well as a powdery or crystalline trehalose prepared from these saccharides, can be used intact, or, if necessary they can be admixed with an excipient, filler and/or binder and formed into granules, spheres, short-rods, plates, cubes and tablets, prior to their use.

The present non-reducing saccharides and relatively-low reducing saccharides containing them, and trehalose prepared from these saccharides have a sweetness which well harmonizes with other materials having sourness, acidness, saltines, astringency, deliciousness and bitterness, and they are highly acid- and heat-resistant. Thus, they can be favorably used in food products in general as a sweetener, taste-improving agent and quality-improving agent.

The present non-reducing saccharides, relatively-low reducing saccharides containing them, and trehalose prepared from these saccharides can be used in seasonings such as amino acids, peptides, soy sauce, powdered soy sauce, "miso", "funmatsu-miso" (a powdered miso), "moromi" (a refined sake)", "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid condiments, mixed seasoning, "mirin" (a sweet sake), "shin-mirin" (a synthetic mirin), table sugar and coffee sugar.

Also, the present non-reducing saccharides, relatively-low reducing saccharides containing them, and trehalose prepared from these saccharides can be favorably used for sweetening "wagashi" (Japanese cakes) such as "senbei" (a rice cracker)", "arare" (a glutinous rice cracker), "okoshi" (a millet-and-rice cracker), "mochi" (a rice paste)"manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castellan and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickled and pickled products such as "fukujin-zuke (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as ham and sausage; products of fish meat such as fish meat ham, fish meat sausage, "kamaboko" (a steamed fish paste), "chikuwa" (a kind of fish paste) and "tenpura" (a Japanese deep-fat fried fish pastefoods)"; "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirinboshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as synthetic sake, wine and liqueurs; soft drinks such as coffee, tea, cocoa, juice, carbonated beverage, sour milk beverage and beverage containing a lactic acid bacterium; instant food products such as instant pudding mix, instant hot cake mix, "sokuseki-shiruko" (an instant mix of adzuki-bean soup with rice cake) and instant soup mix; and beverages such as baby foods, foods for therapy, beverages supplemented with nutrition, peptide foods and frozen foods; as well as for improving the taste and qualities of the aforementioned food-products.

The present non-reducing saccharides, relatively-low reducing saccharides containing them, and trehalose prepared from these saccharides can be used in feeds and pet foods for animals such as domestic animals and poultry, honey bee, silkworm and fish to improve their taste preference. These saccharides and trehalose can be arbitrarily used as a sweetener, taste-improving agent, quality-improving agent and stabilizer in other products in paste and liquid form such as a tobacco, cigarette, dentifrice, lipstick, rouge, lip cream, internal medicine, tablet, troche, cod liver oil in the form of drop, cachou, oral refrigerant, gargle, cosmetic and pharmaceutical.

The non-reducing saccharides, relatively-low reducing saccharides containing them, and trehalose prepared from these saccharides can be used as a quality-improving agent and stabilizer in biologically active substances susceptible to deterioration of their effective ingredients and activities, as well as in health foods and pharmaceuticals containing biologically active substances. Examples of such a biologically active substances are lymphokines such as interferon-α, interferon-β, interferon-γ, tumor necrosis factor-α, tumor necrosis factor-β, macrophage-migration inhibitory factor, colony-stimulating factor, transfer factor and interleukin 2;

hormones such as insulin, growth hormone, prolactin, erythropoietin and follicle-stimulating hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, β-amylase, isoamylase, glucanase and lactase; extracts such as ginseng extract, snapping turtle extract, chlorella extract, aloe extract and propolis extract; and viable microorganisms such as viruses, lactic acid bacteria and yeasts; and other biologically active substances such as royal jelly. By using the present non-reducing saccharides, relatively-low reducing saccharides containing them, and trehalose prepared from these saccharides, the aforementioned biologically active substances are arbitrarily prepared into health foods and pharmaceuticals with a satisfactorily-high stability and quality without fear of losing or inactivating their effective ingredients and activities.

As described above, the methods to incorporate the present non-reducing saccharides, relatively-low reducing saccharides containing them and/or trehalose prepared from these saccharides into the above-mentioned compositions include conventional methods, for example, mixing, kneading, dissolving, melting, soaking, permeating, sprinkling, applying, coating, spraying, injecting, crystallizing and solidifying. These saccharides and trehalose are usually incorporated into the above-mentioned compositions in an amount of 0.1% or higher, preferably, one % or higher, d.s.b.

The following experiments explain the present invention in more detail.

EXPERIMENT 1

Preparation of thermostable non-reducing saccharide-forming enzyme from *Sulfolobus acidocaldarius* ATCC 33909

A liquid nutrient culture medium, consisting of 0.1 w/v % peptone, 0.1 w/v % yeasts extract, 0.2 w/v % ammonium sulfate, 0.05 w/v % potassium phosphate, 0.02 w/v % magnesium sulfate, 0.02 w/v % potassium chloride and water, was prepared. About 100 ml aliquots of the nutrient culture medium were placed in 500-ml Erlenmeyer flasks, autoclaved at 120° C. for 20 minutes to effect sterilization, cooled and adjusted to pH 3.0 by the addition of sulphate, and then inoculated with a stock culture of *Sulfolobus acidocaldarius* ATCC 33909 and incubated at 70° C. for 24 hours under stirring conditions of 130 rpm. The resultant cultures were pooled and used as a first seed culture.

About 5 liter of a fresh preparation of the same nutrient culture medium used in the first seed culture was placed in a 10-liter fermenter, sterilized, cooled to 75° C. and adjusted to pH 3.0, and then inoculated with one v/v % of the first seed culture and incubated at 75° C. for about 48 hours while stirring under aerobic conditions at an aeration of 500 ml/min to obtain a second seed culture.

About 250 liter of a fresh preparation of the same nutrient culture medium used in the first seed culture was placed in a 300-liter fermenter, sterilized, cooled to 75° C. and adjusted to pH 3.0, and then inoculated with one v/v % of the second seed culture and incubated at 75° C. for about 42 hours while stirring under aerobic conditions at an aeration of 100 ml/min. About 170 liter of the resultant culture was filtered with an SF-membrane and centrifuged to recover about 258 g wet cells. The cells thus recovered were suspended in 300 ml of 10 mM phosphate buffer (pH 7.0) and treated with "US 300", a supersonic cell disrupting apparatus commercialized by Nippon Seiki. Co., Ltd., Niigate, Japan, to disrupt cells. The resultant mixture was centrifuged at 10,000 rpm for 30 minutes to obtain an about 300 ml supernatant. To the supernatant was added ammonium sulfate and dissolved to give a saturation degree of 0.7, and the resultant solution was allowed to stand at 4° C. for 24 hours, and centrifuged to obtain a precipitate. The resultant precipitate was dissolved in 10 mM Tris-HCl buffer (pH 8.5), and dialyzed against a fresh preparation of the same hydrochloric acid buffer for 24 hours, and centrifuged to remove insoluble substances. The resultant dialyzed solution (about 600 ml) was divided into 2 portions which were then separately subjected to column chromatography using a column packed with about 350 ml of "DEAE-TOYOPEARL®", an ion exchanger commercialized by Tosoh Corporation, Tokyo, Japan. The objective enzyme adsorbed on the ion exchanger was eluted from the column with a linear gradient buffer supplemented 0.3M to 0M sodium chloride, followed by recovering fractions with enzyme activity which was eluted from the column at about 0.1M sodium chloride. The resultant fractions were dialyzed against a fresh preparation of 10 mM Tris-HCl buffer (pH 8.5) containing 1M ammonium sulfate. The dialyzed solution thus obtained was centrifuged to remove insoluble substances, and the resultant supernatant was subjected to hydrophobic column chromatography using a column packed with 350 ml of "BUTYL-TOYOPEARL®", a hydrophobic gel commercialized by Tosoh Corporation, Tokyo, Japan. The enzyme adsorbed on the gel was eluted from the column with a linear gradient buffer containing 1M to 0M ammonium sulfate, followed by recovering about 440 unit of the enzyme activity contained in the fractions which were eluted from the column supplemented with about 0.8M ammonium sulfate. The partially purified enzyme preparation thus obtained exhibited the specific activity of about 20 units/mg protein.

The partially purified enzyme preparation was dialyzed against a fresh preparation of 10 mM Tris-HCl buffer (pH 8.5) containing 0.2M sodium chloride, and the dialyzed solution was centrifuged to remove insoluble substances. The resultant supernatant was subjected to gel filtration chromatography using "ULTROGEL AcA 44®", a resin for gel filtration commercialized by Sepracor Inc., Marlborough, Mass. 01752, U.S.A., to recover fractions with the enzyme activity, and the resultant fractions were dialyzed against a fresh preparation of 10 mM Tris-HCl buffer (pH 8.5) and centrifuged to remove insoluble substances. The resultant supernatant was subjected to column chromatography using a column packed with 10 ml of "MONO Q®", an ion exchanger commercialized by Pharmacis LKB, Uppsala, Sweden. The enzyme adsorbed on the ion exchanger was eluted from the column with a linear gradient buffer ranging from 0.2M to 0M sodium chloride, followed by recovering about 40 units of the enzyme activity contained in fractions which were eluted from the column at about 0.1M sodium chloride.

A purified preparation of the thermostable non-reducing saccharide-forming enzyme obtained as the above purification, exhibited the specific activity of about 81 units/mg protein, and was determined for purity on electrophoresis using 10% SDS-polyacrylamide gel to exhibit a single protein band, and this revealed that the preparation was an electrophoretically homogeneous enzyme with a relatively-high purity.

EXPERIMENT 2

Physicochemical properties of thermostable non-reducing saccharide-forming enzyme An aqueous solution containing 10 w/v % glucose, maltose, maltotriose, maltotetraose, maltopentaose, maltohexaose or maltoheptaose as a substrate was prepared, and admixed with 2 units/g substrate, d.s.b., of the purified enzyme preparation obtained by the method in Experiment 1, and the resultant mixture was subjected to an enzymatic reaction at 60° C. and pH 5.5 for 48 hours. The reaction mixture was desalted and analyzed on high-performance liquid chromatography (HPLC) using a column packed with "WAKOBEADS WB-T-330®", a product of Wako Pure Chemical Industries Ltd., Tokyo, Japan.

The HPLC procedure was conducted at ambient temperature and a flow rate of 0.5 ml/min of water as an eluent, and "RI-8012®", a differential refractometer commercialized by Tosho Corporation, Tokyo, Japan, was used for analyzing reaction products. The results were in Table 1.

As evident from the results in Table 1, it was revealed that the present purified enzyme formed non-reducing saccharides having a trehalose structure as an end unit which were composed of α-glucosyl trehalose to α-maltopentaosyl trehalose when allowed to act on partial starch hydrolysates having a degree of glucose polymerization of 3 or higher which were composed of maltotriose to maltoheptaose. Also, it was revealed that in addition to the remaining substrate and non-reducing saccharides producible without altering the degree of glucose polymerization, a relatively-small amount of glucose as a hydrolysate of substrate and lower molecular weight maltooligosaccharides as well as non-reducing saccharides prepared from them existed in the reaction mixture, and the present purified enzyme had a slight hydrolytic activity to the non-reducing saccharide-forming activity. The yields of non-reducing saccharides, prepared by allowing the present purified enzyme to act on the substrates, and reducing saccharides prepared from hydrolysates were respectively 30.2% and 27.6% in the case of using maltotriose as a substrate, 65.4% and 18.4% for maltotetraose, about 74–75% and 2–3% for maltopentaose and maltoheptaose having a degree of glucose polymerization 4 to 5, and it was revealed that non-reducing saccharides were formed at a relatively-high yield from maltooligosaccharides having a degree of glucose polymerization of 5 or higher, and also hydrolysates were formed in small quantity. Also, it was revealed that no saccharide was newly formed from glucose and maltose.

TABLE 1

| Substrate | Saccharides in reaction mixture | Saccharide composition (%) |
|---|---|---|
| Glucose | Glucose | 100.0 |
| Maltose | Maltose | 100.0 |
| Maltotriose | Glucose | 9.2 |
|  | Maltose | 18.4 |
|  | Maltotriose | 42.2 |
|  | α-glucosyl trehalose | 30.2 |
| Maltotetraose | Glucose | 6.7 |
|  | Maltose | 2.7 |
|  | Maltotriose | 9.0 |

TABLE 1-continued

| Substrate | Saccharides in reaction mixture | Saccharide composition (%) |
|---|---|---|
|  | Maltotetraose | 16.2 |
|  | α-glucosyl trehalose | 8.2 |
|  | α-maltosyl trehalose | 57.2 |
| Maltopentaose | Glucose | 0.7 |
|  | Maltotetraose | 2.0 |
|  | Maltopentaose | 22.9 |
|  | α-maltosyl trehalose | 0.9 |
|  | α-maltotriosyl trehalose | 73.5 |
| Maltohexaose | Glucose | 0.9 |
|  | Maltopentaose | 2.2 |
|  | Maltohexaose | 23.1 |
|  | α-maltotriosyl trehalose | 5.6 |
|  | α-maltotetraosyl trehalose | 68.2 |
| Maltoheptaose | Glucose | 1.0 |
|  | Maltohexaose | 1.4 |
|  | Maltoheptaose | 23.4 |
|  | α-maltotetraosyl trehalose | 4.2 |
|  | α-maltopentaosyl trehalose | 70.0 |

EXPERIMENT 2-2

Molecular weight

The present enzyme was determined for molecular weight on SDS-polyacrylamide gel electrophoresis according to the method as reported by U. K. Laemmli in "Nature", Vol.227, pp.680–685 (1970) to exhibit an electrophoretically single band corresponding to about 69,000–79,000 daltons. In such an electrophoresis, myosin (200,000 daltons), β-galactosidase (116,250 daltons), phosphorylase (97,400 daltons), serum albumin (66,200 daltons) and ovalbumin (45,000 daltons) were used as a marker/protein.

EXPERIMENT 2-3

Isoelectric point (pI)

The present enzyme was isoelectrophoresed in a polyacrylamide gel containing 2% ampholyte, commercialized by Pharmacia LKB, Uppsala, Sweden. Also, the pH of the resultant gel was adjusted to and the pI of the enzyme was determined to give a pI of about 5.4–6.4.

EXPERIMENT 2-4

Optimum temperature

When incubated for 60 min in 20 mM acetate buffer (pH 5.5) in usual manner, the present enzyme gave an optimum temperature of about 75° C. in FIG. 1.

EXPERIMENT 2-5

Optimum pH

Figure 2:
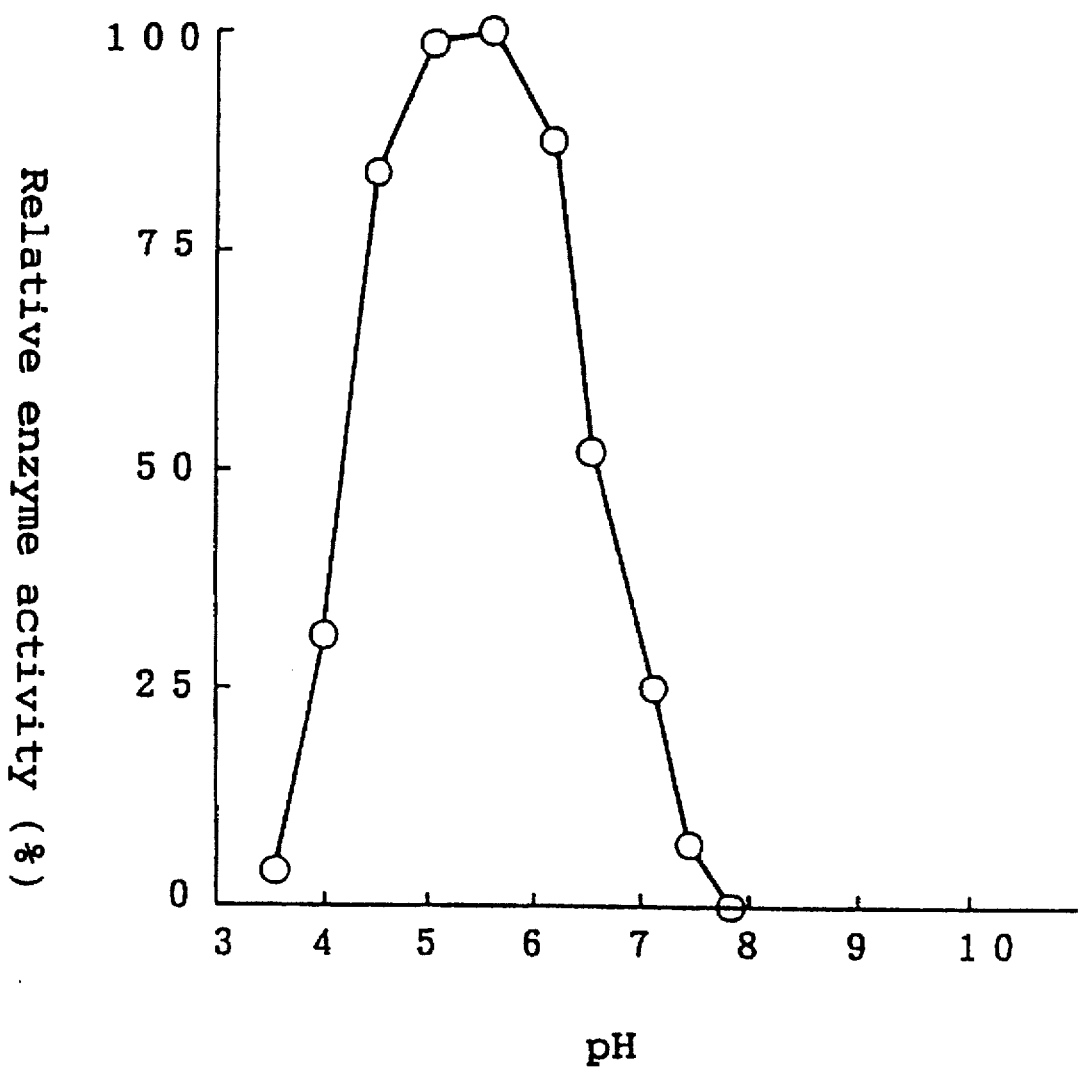
FIG. 2 shows the influence of pH on the activity of the thermostable non-reducing saccharide-forming enzyme of the present invention.

When incubated at 60° C. for 60 min in McIlvaine's buffer having different pHs in usual manner, the present enzyme gave an optimum pH of 5.0–5.5 in FIG. 2.

EXPERIMENT 2-6

Thermal stability

Figure 3:
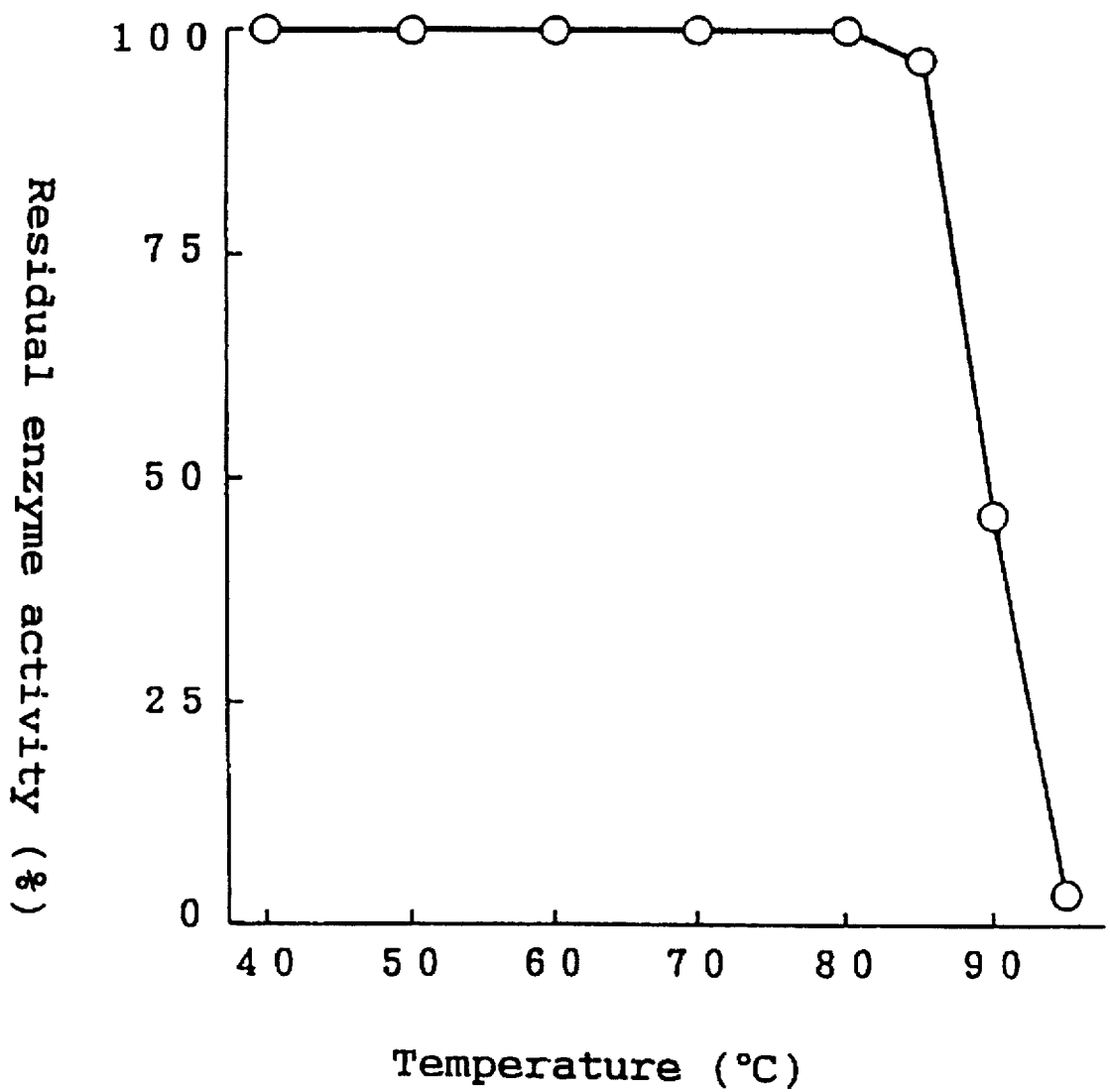
FIG. 3 shows the thermal stability of the thermostable non-reducing saccharide-forming enzyme of the present invention.

When incubated for 60 min in 10 mM phosphate buffer (pH 7.0) in usual manner, the present enzyme was stable up to a temperature of about 85° C. in FIG. 3.

EXPERIMENT 2-7 pH stability

Figure 4:
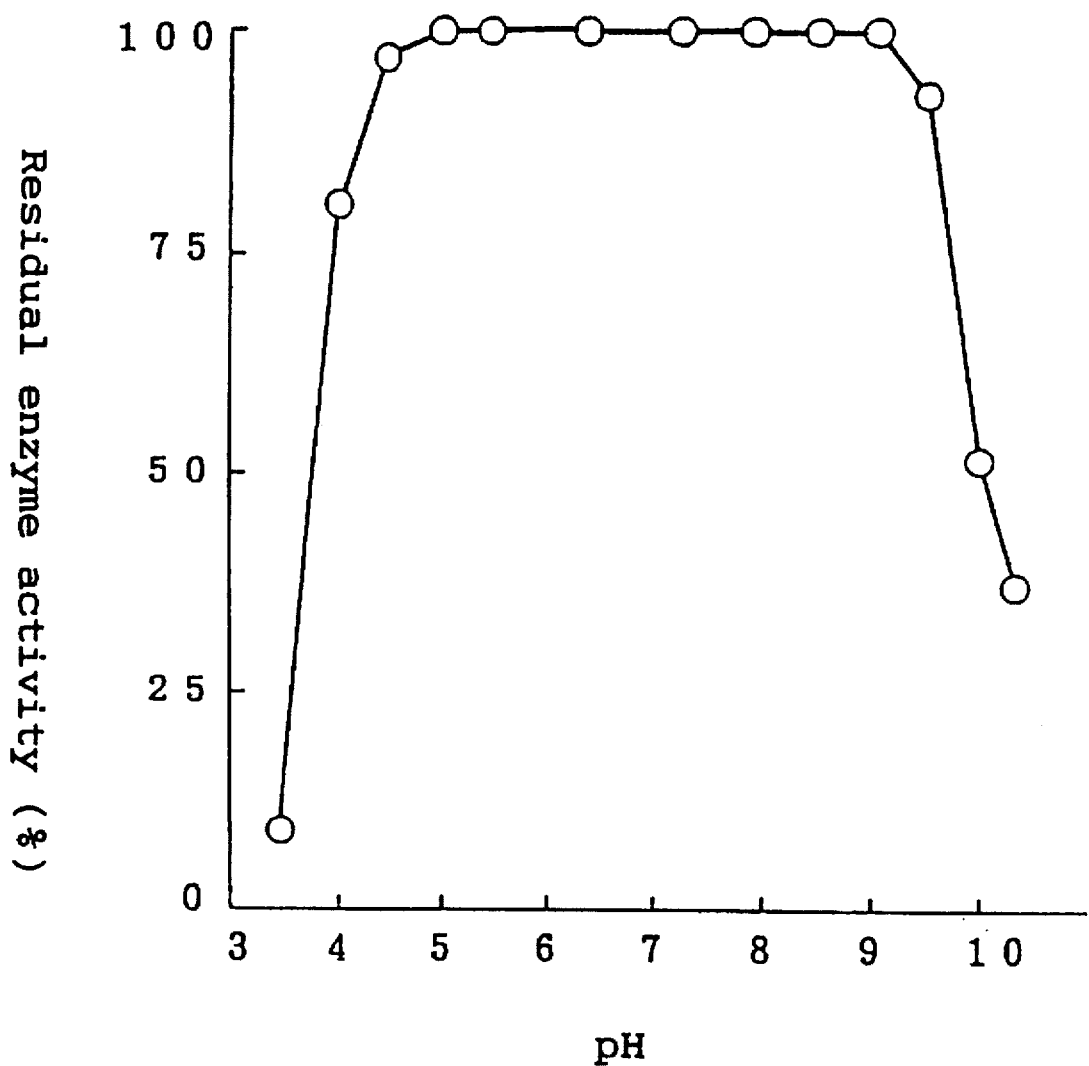
FIG. 4 shows the pH stability of the thermostable non-reducing saccharide-forming enzyme of the present invention.

When incubated at 25° C. for 16 hours in McIlvaine's buffer having different pHs or sodium carbonate-sodium hydrogencarbonate buffer in usual manner, the present enzyme was stable at a pH of about 4.5–9.5 in FIG. 4.

EXPERIMENT 2-8

Amino acid sequence containing N-terminal

Aliquots of a purified thermostable non-reducing saccharide-forming enzyme preparation, obtained by the method in Experiment 1 was dialyzed against distilled water, and about 80 μg protein of each resultant preparation was used as a sample for determining the amino acid sequence containing the N-terminal. The amino acid sequence was analyzed on "MODEL 473A", a protein sequencer, commercialized by Perkin-Elmer Corp., Instrument Div., Norwalk, U.S.A., to reveal the 10 amino acid residues from the N-terminal. The partial amino acid sequence containing the N-terminal was as follows:

Met Ile Ser Ala Thr Tyr Arg Leu Gln Leu   (SEQ ID NO:1)
1              5                    10

EXPERIMENT 3

Preparation of thermostable non-reducing saccharide-forming enzyme from other microorganisms of the genus Sulfolobus A nutrient culture medium was prepared, inoculated with microorganisms, and incubated for 42 hours in a fermenter by the same method in Experiment 1 except that *Sulfolobus acidocaldarius* (ATCC 49426), *Sulfolobus solfataricus* (ATCC 35091) and *Sulfolobus solfataricus* (ATCC 35092) were used as microorganisms in place of *Sulfolobus acidocaldarius* (ATCC 33909). The cells were recovered from about 170 liters of each resultant culture, disrupted with ultrasonic to obtain a supernatant, and the resultant supernatant was salted out with ammonium sulfate, dialyzed, and subjected to an ion-exchange column and hydrophobic column chromatography to obtain a partially purified enzyme preparation, followed by studying its properties. The results were in Table 2.

In accordance with the method in Experiment 2-1, non-reducing saccharides were prepared by using these partially purified enzyme preparations, and studied on their structures to find that, similarly as the thermostable non-reducing saccharide-forming enzyme from *Sulfolobus acidocaldarius* (ATCC 33909), every enzyme preparation formed non-reducing saccharides having a trehalose structure as an end unit and a degree of glucose polymerization of 3 or higher when allowed to act on reducing partial starch hydrolysates having a degree of glucose polymerization of 3 or higher.

TABLE 2

| Microorganism | Enzyme activity in eluate from ion-exchange column (unit) | Optimum temperature (°C.) | Optimum pH | Thermal stability (°C.) | pH stability |
|---|---|---|---|---|---|
| *Sulfolobus acidocaldarius* (ATCC 33909) | 440 | About 75° C. | About 5.0–5.5 | Up to about 85° C. | About 4.5–9.5 |
| *Sulfolobus acidocaldarius* (ATCC 49426) | 370 | About 75° C. | About 5.0–5.5 | Up to about 85° C. | About 4.5–9.5 |
| *Sulfolobus solfataricus* (ATCC 35091) | 210 | About 75° C. | About 5.0–5.5 | Up to about 85° C. | About 4.0–8.5 |
| *Sulfolobus solfataricus* (ATCC 35092) | 95 | About 75° C. | About 5.0–5.5 | Up to about 85° C. | About 4.0–8.5 |

The following Examples A illustrate the preparation of the present non-reducing saccharides, relatively-low reducing saccharides containing them, and trehalose; and Examples B illustrate compositions containing one or more of these saccharides and trehalose.

EXAMPLE A-1

A seed culture of *Sulfolobus acidocaldarius* (ATCC 33909) was inoculated in a nutrient culture medium and incubated by a fermenter for about 42 hours in accordance with the method in Experiment 1. After completion of the incubation, the resultant culture was concentrated with an SF-membrane and centrifuged to recover cells. The cells thus obtained were disrupted with ultrasonic, and from the suspension an supernatant was prepared, salted out with ammonium sulfate, dialyzed, and subjected to an ion-exchange column and hydrophobic column chromatography to obtain an enzyme solution containing 18.0 units/ml of a partially purified enzyme preparation having a specific activity of about 20 units/mg protein. The suspension of potato starch having a concentration of 6 w/v % was gelatinized by heating, adjusted to pH 4.5 and 50° C., admixed with 2,500 units/g starch of isoamylase commercialized by Hayashibara Biochemical Laboratories, Inc., Okayama, Japan, and subjected to an enzymatic reaction for 20 hours. The resultant mixture was adjusted to pH 6.5, autoclaved at 120° C. for 10 min, cooled to 60° C., admixed with 30 units/g starch of "TERMAMYL 60L", α-amylase commercialized by Novo Industri A/S, Copenhagen, Denmark, and subjected to an enzymatic reaction for 24 hours. The reaction mixture was autoclaved at 120° C. for 20 min, cooled to 65° C., adjusted to pH 5.5, admixed with one unit/g starch of the above thermostable non-reducing saccharide-forming enzyme, and subjected to an enzymatic reaction for 96 hours. The resultant mixture was kept at 97° C. for 30 min, cooled and filtered. The resultant filtrate was in usual manner decolored with an activated charcoal, and purified by desalting it with ion-exchange resins in H- and OH-form. The resultant solution was concentrated into a syrup with a concentration of about 70 w/v % in a yield of about 90%. The product exhibits a DE 24.6, and contains as a non-reducing saccharide 12.0% α-glucosyl trehalose, 5.5% α-maltosyl trehalose, 29.9% α-maltotriosyl trehalose, 1.5% maltotetraosyl trehalose and 2.2% α-maltopentaosyl trehalose, d.s.b. The product has a mild and high-quality sweetness, as well as an adequate viscosity and moisture-retaining ability, and these properties render it arbitrarily useful in food products, cosmetics and pharmaceuticals as a sweetener, taste-improving agent, quality-improving agent, stabilizer and filler.

EXAMPLE A-2

A saccharide solution as a feed solution, obtained by the method in Example A-1, was fractionated on a column packed with "XT-1016 (polymerization degree of 4%, $Na^+$-form)", a strongly-acidic cation exchange resin commercialized by Tokyo Organic Chemical Industries Ltd., Tokyo, Japan to increase the content of non-reducing sccharides. The procedure was as follows: The resin was packed in 4 jacketed-stainless steel columns having an inner diameter of 5.4 cm, and the columns were cascaded in series to give a total gel-bed depth of 20 m. The columns were heated to give the inner column temperature of 55° C., and fed with 5 v/v % of the saccharide solution against the resin while keeping at the temperature, and the saccharide solution was fractionated by feeding to the columns with 55° C. hot water at SV 0.13 to elute fractions rich in glucose and maltose, followed by recovering fractions rich in non-reducing saccharides. The fractions rich in non-reducing saccharides were pooled, purified, concentrated, dried in vacuo, and pulverized to obtain a powdery product containing non-reducing saccharides in a yield of about 64%, d.s.b. The product exhibits a DE 4.8, and contains as a non-reducing saccharide 18.2% α-glucosyl trehalose, 7.9% α-maltosyl trehalose, 46.6% α-maltotriosyl trehalose, 2.3% maltotetraosyl trehalose and 3.4% α-maltopentaosyl trehalose, d.s.b. Similarly as the product in Example A-1, the product has a mild and high-quality sweetness, as well as an adequate viscosity and moisture-retaining ability, and these properties render it arbitrarily useful in food product, cosmetics and pharmaceuticals as a sweetener, taste-improving agent, quality-improving agent, stabilizer and filler.

EXAMPLE A-3

Thirty-three % suspension of corn starch, d.s.b., was admixed with calcium carbonate to give the final concentration of 0.1%, d.s.b., and the resultant mixture was adjusted to pH 6.5, admixed with 0.2%, d.s.b., per g starch of "TERMAMYL 60 L", α-amylase commercialized by Novo Industri A/S, Copenhagen, Denmark, and subjected to an enzymatic reaction at 95° C. for 15 min. The resultant mixture was autoclaved at 120° C. for 10 min, cooled to 55° C., admixed with 5 units/g starch of maltotetraose-forming amylase as disclosed in Japanese Patent Laid-Open No.240, 783/63, commercialized by Hayashibara Biochemical Laboratories, Inc., Okayama, Japan, and subjected to an enzymatic reaction for 6 hours. The resultant mixture was admixed with 30 units/g starch of "α-amylase 2A", α-amylase commercialized by Ueda Chemical Co., Ltd., Osaka, Japan, and subjected to an enzymatic reaction at 65° C. for 4 hours. The resultant mixture was autoclaved at 120° C. for 10 min, cooled to 45° C., adjusted to pH 5.5, admixed with 2 units/g starch of a thermostable non-reducing saccharide-forming enzyme obtained by the method in Example A-1, and subjected to an enzymatic reaction for 48 hours. The resultant mixture was kept at 97° C. for 30 min, cooled and filtered to obtain a filtrate which was then decolored with an activated charcoal in usual manner, and purified by desalting it with ion-exchange resins in H- and OH-form, followed by concentrating the resultant solution to obtain a 70% syrup in a yield of about 90%, d.s.b. The product exhibits a DE 17.1, and contains as a non-reducing saccharide 8.9% α-glucosyl trehalose, 29.3% α-maltosyl trehalose, 0.8% α-maltotriosyl trehalose, 0.7% maltotetraosyl trehalose and 0.7% α-maltopentaosyl trehalose, d.s.b. The product has a mild and high-quality sweetness, as well as an adequate viscosity and moisture-retaining ability, and these properties render it arbitrarily useful in food product, cosmetics and pharmaceuticals as a sweetener, taste-improving agent, quality-improving agent, stabilizer and filler.

EXAMPLE A-4

A saccharide solution as a feed solution, obtained by the method in Example A-3, was column chromatographed in accordance with the method in Example A-2 except that "50W-X4 ($Mg^{++}$-form)", a strongly-acidic cation exchange resin commercialized by Dow Chemical Co., Midland, Mich., USA, was used as a resin for fractionation to increase the content of α-maltosyl trehalose and to obtain a α-maltosyl trehalose rich fraction. The fraction was purified, concentrated and spray dried to obtain a powdery product rich in non-reducing saccharides in a yield of about 41%, d.s.b. The product contains as a non-reducing saccharide 10.9% α-glucosyl trehalose, 61.3% α-maltosyl trehalose and 1.0% α-maltotriosyl trehalose, exhibits a DE 2.5, and have a relatively-low reducibility. Similarly as the product in Example A-3, the product has a mild and high-quality sweetness, as well as an adequate viscosity and moisture-retaining ability, and these properties render it arbitrarily useful in food product, cosmetics and pharmaceuticals as a sweetener, taste-improving agent, quality-improving agent, stabilizer and filler.

EXAMPLE A-5

Forty parts by weight of "PINE-DEX #4", a partial starch hydrolysate commercialized by Matsutani Chemical Ind., Tokyo, Japan, was dissolved in 60 parts by weight of water, and the resultant solution was heated to 65° C., adjusted to pH 5.5, admixed with one unit/g partial starch hydrolysate of a thermostable non-reducing saccharide-forming enzyme prepared by the method in Example A-1, and subjected to an enzymatic reaction for 96 hours. Thereafter, the reaction mixture was heated at 97° C. for 30 min to inactivate the remaining enzyme, diluted to give a concentration of about 20%, d.s.b., admixed with 10 units/g partial starch hydrolysate of "GLUCOZYME", glucoamylase commercialized by Nagase Biochemicals, Ltd., Kyoto, Japan, and subjected to an enzymatic reaction for 10 hours, followed by heating the resultant mixture to inactivate the remaining enzyme. The mixture thus obtained was in usual manner decolored with an activated charcoal, desalted with an ion-exchange resin, and concentrated to give a concentration of about 60%, d.s.b. The saccharide solution thus obtained contained 30.1% trehalose, d.s.b. The saccharide solution was column chromatographed in accordance with the method in Example A-2 except that "CG 6000 (Na⁺-form)" a strongly-acidic cation exchange resin commercialized by Japan Organo Co., Ltd., Tokyo, Japan, was used as a resin for fractionation, followed by recovering a trehalose-rich fraction. The fraction contained about 97% trehalose, d.s.b., and it was concentrated into an about 75% solution which was then placed in a crystallizer, admixed with a seed crystal and gradually cooled to obtain a massecuite with a degree of crystallization of about 45%. The massecuite was sprayed from a nozzle equipped on the top of a spraying tower, at a pressure of 150 kg/cm². In the spraying step, the massecuite was simultaneously ventilated with 85° C. hot air from the top of the spraying tower, and the resultant crystalline powder was collected on a metal wire netting conveyer provided on the basement of the spraying tower, gradually conveyed out from the tower while a stream of 40° C. air was passing upwards through the metal wire netting. The resultant crystalline powder was injected in an aging tower and aged for 10 hours while sending hot air thereto to complete the crystallization and drying, followed by recovering a powdery hydrous crystalline trehalose. The product exhibits no substantial hygroscopicity and has a satisfiable handleability, and these properties render it arbitrarily useful in food products, cosmetics and pharmaceuticals as a sweetener, taste-improving agent, quality-improving agent, stabilizer and filler.

EXAMPLE A-6

A seed culture of *Sulfolobus solfataricus* (ATCC 35091) was inoculated in a nutrient culture medium and incubated by a fermenter for about 42 hours in accordance with the method in Experiment 3. After completion of the incubation, the resultant culture was concentrated with an SF-membrane and centrifuged to recover cells, which were then disrupted with ultrasonic to obtain a supernatant. The resultant supernatant was salted out with ammonium sulfate, dialyzed, and subjected to an ion-exchange column and hydrophobic column chromatography to obtain an enzyme solution containing 19.0 units/ml of a partially purified enzyme preparation having a specific activity of about 18 units/mg protein. In accordance with the method in Example A-3, the suspension of potato starch having a concentration of 30% was treated with "TERMAMYL 60L", α-amylase commercialized by Novo Industri A/S, Copenhagen, Denmark, a maltotetraose forming amylase commercialized by Hayashibara Biochemical Laboratories, Inc., Okayama, Japan, and "α-amylase 2A", α-amylase commercialized by Ueda Chemical Co., Tokyo, Japan, and autoclaved at 120° C., cooled to 65° C., admixed with 2 units/g starch of the above thermostable non-reducing saccharide-forming enzyme, and subjected to an enzymatic reaction for 64 hours. The resultant mixture was kept at 97° C. for 30 min to inactivate the remaining enzyme. In accordance with the method in Example A-5, the resultant solution was subjected to the action of "GLUCOZYME", glucoamylase commercialized by Nagase Biochemicals, Ltd., decolored, desalted and concentrated into an about 60% solution. The saccharide solution thus obtained contained about 23% trehalose, d.s.b. In accordance with the method in Example A-5, the saccharide solution was fractionated on column chromatography using a strongly-acidic action-exchange resin to obtain fractions rich in trehalose. The fractions containing about 95% trehalose, d.s.b., were pooled, placed in a vessel and boiled down under a reduced pressure into a syrup with a moisture content of about 4.0%. The syrup was placed in a crystallizer and admixed with one % of anhydrous crystalline trehalose, as a seed crystal, with respect to the syrup, d.s.b., followed by crystallizing the syrup at 95° C. for 5 min while stirring. The resultant was transferred to an aluminum container and aged at 100° C. for 6 hours to form a block. The resultant block was pulverized by a cutting machine and subjected to a fluidized-bed drying to obtain a powdery anhydrous crystalline trehalose with a moisture content of about 0.3 w/w %. The product can be arbitrarily used in hydrous matters such as food products, cosmetics and pharmaceuticals, and their material and intermediates as a desiccant, as well as a white powdery sweetener with a high-quality and mild sweetness.

EXAMPLE B-1

Sweetener

To one part by weight of a powdery product rich in non-reducing saccharides, obtained by the method in Example A-4, was homogeneously added 0.01 part by weight of "αG Sweet®", α-glycosyl stevioside commercialized by Toyo Sugar Refining Co., Ltd., Tokyo, Japan, and 0.01 part by weight of "Aspartame", L-aspartyl-L-phenylalanine methylester commercialized by Ajinomoto Co., Ltd., and the mixture was fed to a granulator to obtain a granular sweetener. The product has a satisfactory sweetness and a 2-fold higher sweetening power of sucrose, and the caloric value is lowered to about ½ of that of sucrose. The product having a satisfiable stability neither affects nor decomposes other sweeteners with a relatively-high sweetness when mixed with them, and because of this it can be suitably used as a low-caloric sweetener for low-caloric food products for fat persons and diabetics who are restricted to a reduced calorie intake. The product scarcely forms acid and insoluble glucans when dental carries-inducing microorganisms act on it, and this renders it useful for sweetening food products directed to the prevention of dental carries.

EXAMPLE B-2

Hard candy

One hundred parts by weight of 55% sucrose solution was mixed with 30 parts by weight of a syrup containing non-reducing saccharides, obtained by the method in Example A-3, and the resultant mixture was concentrated by heating it in vacuo until the moisture content lowered to below 2%. The concentrated solution was admixed with one part by weight of citric acid and adequate amounts of a lemon flavor and a coloring agent, and the resultant mixture was formed in usual manner to obtain the desired product. The product is a high-quality hard candy having a satisfiable taste and biting property, as well as having no fear of changing the form and causing crystallization of sucrose.

EXAMPLE B-3

Chewing gum

Three parts by weight of gum base was melted by heating until it softened, and the resultant was admixed with 4 parts by weight of sucrose and 3 parts by weight of a hydrous crystalline trehalose powder obtained by the method in Example A-5, and further admixed with adequate amounts of a flavor and a coloring agent. The resultant mixture was kneaded by a roll in usual manner, formed and packed to obtain the desired product. The product is a chewing gum having a satisfiable texture and taste.

EXAMPLE B-4

Sweetened condensed milk

Three parts by weight of a syrup containing non-reducing saccharides obtained by the method in Example A-1 and one part by weight of sucrose were dissolved in 100 parts by weight of fresh milk, and the resultant solution was sterilized by heating with a plate heater, and condensed into a 70% solution, followed by aseptically canning the resultant into the desired product. The product with a mild sweetness and a satisfiable taste can be arbitrarily used as a seasoning for baby foods, fruit, coffee, cocoa and tea.

EXAMPLE B-5

Beverage containing lactic acid bacteria

One hundred and seventy-five parts by weight of defatted milk, 80 parts by weight of a high non-reducing saccharide content powder prepared by the method in Example A-2, and 50 parts by weight of a high lactosucrose content powder disclosed in Japanese Patent Laid-Open No.281,795/92 were dissolved in 1,200 parts by weight of water, and the resultant solution was sterilized by heating at 65° C. for 30 min, cooled to 40° C., admixed in usual manner with 30 parts by weight of lactic acid bacteria as a starter, and incubated at 37° C. for 8 hours to obtain a beverage containing lactic acid bacteria. The product is a beverage containing lactic acid bacteria with a satisfiable taste and flavor. The product containing oligosaccharides stably retains lactic acid bacteria and promotes the growth of bifid bacteria.

EXAMPLE B-6

Powdered juice

Thirty-three parts by weight of a powdered orange juice prepared by spray drying was mixed to homogeneity under stirring conditions with 50 parts by weight of a powder rich in non-reducing saccharides obtained by the method in Example A-2, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan, and an adequate amount of a powdered flavor. The resultant mixture was pulverized, fed to a fluidized-bed granulator and granulated for 30 min by spraying it with a syrup containing non-reducing saccharides as a binder obtained by the method in Example A-1 while sending to the contents 40° C. air at a flow amount of 150 m³. The resultant granules were weighed and packaged to obtain the desired product. The product contains 30% orange juice, d.s.b. The product was stable for a relatively-long period of time without giving an unsatisfiable taste and smell.

EXAMPLE B-7

Custard cream

One hundred parts by weight of corn starch, 100 parts by weight of a syrup containing non-reducing saccharides obtained by the method in Example A-3, 80 parts by weight of maltose, 20 parts by weight of sucrose, and one party by weight of salt were mixed to homogeneity. The resultant mixture was admixed with 280 parts by weight of egg, and gradually added with 1,000 parts by weight of a boiling milk. The mixture thus obtained was continued stirring while heating, and the heating was stopped when the corn starch in the mixture was completely gelatinized to give the whole contents semitransparent, followed by cooling the resultant and adding thereto an adequate amount of a vanilla flavor. The resultant mixture was weighed, injected and packaged to obtain the desired product. The product has a smooth surface and gloss, as well as a mild taste and sweetness.

EXAMPLE B-8

An (beans paste)

Ten parts by weight of adzuki beans as a material was boiled by the addition of water in usual manner, followed by removing the astringency and harshness of the beans, as well as water-soluble impurities, to obtain about 21 kg "adzuki-tsubu-an". To the resultant was added 14 parts by weight of sucrose, 5 parts by weight of a syrup containing non-reducing saccharides obtained by the method in Example A-4, and 4 parts by weight of water, and the resultant mixture was boiled, admixed with a small amount of salad oil, and carefully kneaded up so as not to paste the beans. Thus, the desired product was obtained in a yield of about 35 kg. The product free from discoloration induced by boiling has a satisfiable taste and flavor, and these render it useful as a material an for bean-jam buns, buns with bean-jam filling, dumplings, bean-jam-filled wafers, sherbets and ice creams.

EXAMPLE B-9

Bread

One hundred parts by weight of wheat powder, 2 parts by weight of yeast, 5 parts by weight of sugar, one part by weight of a powder containing non-reducing saccharides obtained by the method in Example A-2, 0.1 part by weight of inorganic yeast food were kneaded with water in usual manner to effect fermentation at 26° C. for 2 hours, and further aged for 30 min, followed by baking up the resultant. The product is a high-quality bread having a satisfiable hue and rising, as well as a satisfiable elasticity and mild sweetness.

EXAMPLE B-10

Ham

To one thousand parts by weight of ham meat slices was added and ground to homogeneity 15 parts by weight of salt and 3 parts by weight of potassium nitrate, and the resultant slices were piled up and allowed to stand overnight in a cold-storage room. Thereafter, the resultant slices were first soaked for 7 days in a cold-storage room in a salt solution consisting of 500 parts by weight of water, 100 parts by weight of salt, 3 parts by weight of potassium nitrate, 40 parts by weight of a powder rich in non-reducing saccharides prepared by the method in Example A-4, and an adequate amount of a peppermint, then washed with cold water in usual manner, tied up, smoked, cooked, cooled and packaged to obtain the desired product. The product is a high-quality ham having a satisfiable hue, taste and flavor.

EXAMPLE B-11

Powdery peptide

One part by weight of 40% "Hinute S", a peptide solution of edible soy beans commercialized by Fuji Oil Co., Ltd., Tokyo, Japan, was admixed with 2 parts by weight of a powder containing hydrous crystalline trehalose prepared by the method in Example A-5, and the resultant mixture was placed in a plastic vessel, dried in vacuo at 50° C., and pulverized to obtain a powdery peptide. The product having a satisfiable taste and flavor can be arbitrarily used as a material for confectioneries such as premixes, sherbets and ice creams, as well as baby foods and therapeutic nutrition in the form of oral and intubation feedings.

EXAMPLE B-12

Powdery egg yolk

Egg yolks prepared from fresh eggs were sterilized at 60°–64° C. by a plate heater, and the resultant liquid was admixed with 4 parts by weight of a powdery anhydrous crystalline trehalose prepared by the method in Example A-6 with respect to one part by weight of the liquid. The resultant mixture was transferred to a vessel, allowed to stand overnight to form a block while the anhydrous crystalline trehalose was allowing to convert into hydrous crystalline trehalose. The block thus obtained was pulverized by a cutting machine to obtain a powdery egg yolk. The product can be arbitrarily used as a material for confectioneries for premixes, sherbets, ice cream and emulsifiers, as well as baby foods and therapeutic nutrition in the form of oral and intubation feedings. The product can be also used as a skin refiner and hair restorer.

EXAMPLE B-13

Cosmetic cream

Two parts by weight of polyoxyethylene glycol monostearate, 5 parts by weight of glyceryl monostearate, self-emulsifying, 2 parts by weight of a powder rich in non-reducing saccharides obtained by the method in Example A-2, one part by weight of α-glycosyl rutin, one part by weight of liquid petrolatum, 10 parts by weight of glyceryl tri-2-ethylhexanoate, and an adequate amount of an antiseptic were dissolved by heating in usual manner. The resultant solution was admixed with 2 parts by weight of L-lactic acid, 5 parts by weight of 1,3-butylene glycol and 66 parts by weight of refined water, and the resultant mixture was emulsified by a homogenizer and admixed with an adequate amount of a flavor while stirring to obtain a cosmetic cream. The product exhibits an antioxidant activity and has a relatively-high stability and these render it arbitrarily useful as a high-quality sunscreen, skin-refining agent and skin-whitening agent.

EXAMPLE B-14

Solid pharmaceutical

To a column of an immobilized anti-human interferon-α antibody was fed in usual manner a natural human interferon-α preparation, commercialized by Hayashibara Biochemical Laboratories Inc., Okayama, Japan to adsorb the interferon-α, and fed with a buffer containing calf serum albumin as a stabilizer, followed by removing an excessive amount of the albumin. Thereafter the interferon-α was eluted with a physiological saline containing 5% of a powdery hydrous crystalline trehalose, d.s.b., obtained by the method in Example A-5, while varying the pH of the physiological saline. The resultant eluate was filtered by a membrane, and the filtrate was dehydrated by about 20-fold volumes of "FINETOSE®", an anhydrous crystalline maltose powder commercialized by Hayashibara Shoji Inc., Okayama, Japan, followed by pulverizing the resultant dehydrated product and tabletting the resultant by a tabletting machine into tablets containing about 150 units of the natural human interferon-α per one tablet, 200 mg weight. The product can be orally administered as a sublingual tablet to patients at a dose of 1–10 tablets/adult/day, and arbitrarily used to treat viral diseases, allergys, rheumatisms, diabetes and malignant tumors. More particularly, the product can be suitably used as a therapeutic agent for AIDS and hepatitis, the number of patients of which has been remarkably increased. The trehalose and anhydrous crystalline maltose incorporated in the product act as a stabilizer, so that the natural human interferon-α is well retained its activity for a relatively-long period of time even at an ambient temperature.

EXAMPLE B-15

Sugar coated tablet

A crude tablet as a core, 150 mg weight, was coated with a solution consisting of 40 parts by weight of a powdery hydrous crystalline trehalose obtained by the method in Example A-5, 2 parts by weight of pullulan having an average molecular weight of 200,000, 30 parts by weight of water, 25 parts by weight of talc, and 3 parts by weight of titanium oxide until the total weight reached to about 230 mg, and the resultant was further coated with a solution consisting of 65 parts by weight of a fresh preparation of the same powdery hydrous crystalline trehalose, one part by weight of pullulan, and 34 parts by weight of water, and glossed with a liquid wax to obtain a sugar coated tablet having a satisfiable gloss and appearance. The product has a relatively-high shock tolerance and retains its high quality for a relatively-long period of time.

EXAMPLE B-16

Intubation feeding

A composition consisting of 500 parts by weight of a powder hydrous crystalline trehalose obtained by the method in Example A-5, 270 parts by weight of dried yolk, 209 parts by weight of defatted milk, 4.4 parts by weight of sodium chloride, 1.8 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotine amide was prepared, and the composition was divided into 25 g aliquot in small moistureproof laminated aluminum packs which were then heat-sealed. One pack of the product is dissolved in about 150–300 ml water and the resultant solution is usable as an a liquid supplemental nutrition parenterally administrable to the nasal cavity, stomach or intestine.

EXAMPLE B-17

Traumatic oniment

Two hundred parts by weight of powder hydrous crystalline trehalose obtained by the method in Example A-5 and 300 parts by weight of crystalline maltose were admixed with 50 parts by weight of methanol containing 3 parts by weight of iodine, and the resultant was mixed with 200 parts by weight of 10 w/v % pullulan to obtain a traumatic ointment which has an appropriate extensity and adhesiveness. The product shortens a therapeutic period and cure traumas without a scar by reason that the iodine incorporated in the product exhibits sterilizing effects and also the trehalose incorporated in the product supplements nutrition into traumas.

As evident from above, the present novel thermostable non-reducing saccharide readily realizes an enzymatic reaction at the temperature of over 55° C. wherein partial starch hydrolysates are converted at a satisfactorily-high yield into non-reducing saccharides having the same degree of glucose polymerization as that of the partial starch hydrolysates without a fear of contamination. The non-reducing saccharides, which can be readily separated and purified, and relatively-low reducing saccharides containing them, as well as trehalose prepared from these saccharides, have a satisfiable stability, quality and mild sweetness. These non-reducing saccharides, relatively-low reducing saccharides containing them, and trehalose prepared from these saccharides can be arbitrarily used in compositions such as food products, cosmetics and pharmaceuticals as a sweetener, taste-improving agent, quality-improving agent, stabilizer and filler.

Thus, the present invention provides a novel technique to prepare in an industrial-scale and at a relatively-low cost non-reducing saccharides having a trehalose structure as an end unit, which could not have been readily obtained in spite of their great demands, by using reducing partial starch hydrolysates prepared from starch as a cheap and abundant source, as well as to prepare relatively-low reducing saccharides containing the non-reducing saccharides, and trehalose prepared from these saccharides. The present invention has a great influence on the fields such as food-, cosmetic- and pharmaceutical-industries, as well as forestry, fisheries, and agricultural-, livestock- and chemical-industries. Thus, the influence of the present invention on these fields is unfathomable.

While there has been described what is at present considered to be the preferred embodiments of the invention, it will be understood the various modifications may be made therein, and it is intended to cover in the appended claims all such modifications as fall within the true spirit and scope of the invention.

6. The purified enzyme of claim 1, which has the following physicochemical properties:
(1) Action
Without requiring trehalose as a substrate, forming a non-reducing saccharide, having a trehalose structure as an end unit and consisting of trehalose and glucose units, when allowed to act on one or more reducing partial starch hydrolysates having a degree of glucose polymerization of at least 3;
(2) Molecular weight
About 69,000 to 79,000 daltons on sodium dodecyl sulfate polyacrylamide gel electrophoresis (SDS-PAGE);
(3) Isoelectric point (pI)
About 5.4 to 6.4 on isoelectrophoresis using ampholyte;
(4) Optimum temperature
About 75° C. when incubated at pH 5.5 for 60 min;
(5) Optimum pH
About 5.0 to 5.5 when incubated at 60° C. for 60 min;
(6) Thermal stability
Retaining at least about 95% of its activity at a temperature of about 85° C. when incubated at pH 7.0 for 60 min; and
(7) pH stability
Retaining at least about 75% of its activity at a pH in the range of about 4.0 to 9.5 when incubated at 25° C. for 16 hours.

We claim:
1. A purified enzyme which forms, without requiring trehalose as a substrate, a non-reducing saccharide having a trehalose structure as an end unit and consisting of trehalose and glucose units when allowed to act on a reducing partial starch hydrolysate, wherein the purified enzyme is not inactivated at a temperature in the range of 55°–70° C.

2. The purified enzyme of claim 1, wherein said reducing partial starch hydrolysate is one or more reducing partial starch hydrolysates having a degree of glucose polymerization of at least 3.

3. The purified enzyme of claim 1, which retains at least about 95% of its activity at a temperature of about 85° C. when incubated at pH 7.0 for 60 min.

4. The purified enzyme of claim 1, which is derived from a microorganism.

5. The purified enzyme of claim 4, wherein said microorganism is a member selected from the group consisting of those of the genus Sulfolobus and mutants thereof.

7. A process for preparing the enzyme of claim 1, which comprises culturing in a nutrient culture medium a microorganism capable of producing said enzyme, and recovering the said enzyme from the resultant culture.

8. The process of claim 7, wherein said microorganism is a member selected from the group consisting of those of the genus Sulfolobus and mutants thereof.

9. A process for producing a non-reducing saccharide having a trehalose structure as an end unit and consisting of trehalose and glucose units which comprises:
(a) allowing the enzyme of claim 1 to act on a solution containing a reducing partial starch hydrolysate as a substrate to form said non-reducing saccharide; and
(b) purifying the resultant solution to obtain said non-reducing saccharide.

10. The process of claim 9, wherein said reducing partial starch hydrolysate is one or more reducing partial starch hydrolysates having a degree of glucose polymerization of at least 3.

11. The process of claim 10, wherein said reducing partial starch hydrolysates are obtainable by the partial hydrolysis of starch.

12. The process of claim 9, wherein the resultant solution in step (b) is further subjected to column chromatography using a strongly-acidic cation-exchange resin to increase the content of said non-reducing saccharide.

13. A process for preparing a saccharide composition which comprises preparing the non-reducing saccharide according to the process of claim 9 and then incorporating the non-reducing saccharide into other saccharides.

14. A process for preparing a food product which comprises preparing the saccharide composition according to the process of claim 13 and then incorporating the saccharide composition into a food material.

15. A process for preparing a cosmetic which comprises preparing the saccharide composition according to the process of claim 13 and then incorporating the saccharide composition into a cosmetically-acceptable carrier.

16. A process for preparing a pharmaceutical which comprises preparing the saccharide composition according to the process of claim 13 and then incorporating the saccharide composition into a pharmaceutically-acceptable carrier.

17. A process for preparing trehalose which comprises:
 (a) allowing the enzyme of claim 1 to act on a solution containing a reducing partial starch hydrolysate as a substrate to form a non-reducing saccharide having a trehalose structure as an end unit and consisting of trehalose and glucose units;
 (b) allowing glucoamylase or α-glucosidase to act on the formed non-reducing saccharide to form trehalose; and
 (c) recovering the resultant solution containing trehalose together with intact reducing partial starch hydrolysate.

18. The process of claim 17, wherein said reducing partial starch hydrolysate is a member selected from the group consisting of reducing partial starch hydrolysates having a degree of glucose polymerization of at least 3.

19. The process of claim 17, wherein said trehalose is a member selected from the group consisting of hydrous crystalline trehalose, anhydrous crystalline trehalose, and mixtures thereof.

20. The process of claim 17, wherein the resultant solution in step (c) is further subjected to column chromatography using a strongly-acidic cation-exchange resin to increase the content of trehalose.

21. A process for preparing a food product which comprises preparing trehalose according to the process of claim 17 and then incorporating the trehalose into a food material.

22. A process for preparing a cosmetic which comprises preparing trehalose according to the process of claim 17 and then incorporating the trehalose into a cosmetically-acceptable carrier.

23. A process for preparing a pharmaceutical which comprises preparing trehalose according to the process of claim 17 and then incorporating the trehalose into a pharmaceutically-acceptable carrier.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Met  Ile  Ser  Ala  Thr  Tyr  Arg  Leu  Gln  Leu
1              5                        10